(12) United States Patent
Ben-Ami

(10) Patent No.: US 10,772,647 B2
(45) Date of Patent: Sep. 15, 2020

(54) DEVICE AND METHOD FOR REMOVING OCCLUSIONS IN A BIOLOGICAL VESSEL

(71) Applicant: Triticum Ltd., Ramat-HaSharon (IL)

(72) Inventor: Doron Jacob Ben-Ami, Ramat-HaSharon (IL)

(73) Assignee: Triticum Ltd., Ramat-HaSharon (IL)

( * ) Notice: Subject to any disclaimer, the term of this patent is extended or adjusted under 35 U.S.C. 154(b) by 94 days.

(21) Appl. No.: 15/528,110

(22) PCT Filed: Jan. 25, 2016

(86) PCT No.: PCT/IL2016/050073
§ 371 (c)(1),
(2) Date: May 19, 2017

(87) PCT Pub. No.: WO2016/120864
PCT Pub. Date: Aug. 4, 2016

(65) Prior Publication Data
US 2017/0311966 A1    Nov. 2, 2017

Related U.S. Application Data

(60) Provisional application No. 62/108,602, filed on Jan. 28, 2015.

(51) Int. Cl.
*A61B 17/22*    (2006.01)
*A61B 17/00*    (2006.01)
*A61B 17/32*    (2006.01)

(52) U.S. Cl.
CPC .......... *A61B 17/22031* (2013.01); *A61B 2017/00858* (2013.01); *A61B 2017/22034* (2013.01); *A61B 2017/320012* (2013.01)

(58) Field of Classification Search
CPC .... A61B 17/22031; A61B 2017/00858; A61B 2017/22034; A61B 2017/320012
See application file for complete search history.

(56) References Cited

U.S. PATENT DOCUMENTS

| 4,643,184 A | 2/1987 | Mobin-Uddin |
| 4,765,332 A | 8/1988 | Fischell et al. |

(Continued)

FOREIGN PATENT DOCUMENTS

| CA | 2571343 | 2/2006 |
| CN | 1216929 | 5/1999 |

(Continued)

OTHER PUBLICATIONS

Chiu, Hecht, Duong, Wu, Tawil. Permeability of Three-Dimensional Fibrin Constructs Corresponding to Fibrinogen and Thrombin Concentrations. Department of Bioengineering UCLA. 2012:1(1). DOI:10,1089/biores.2012.0211 (Year: 2012).*

(Continued)

*Primary Examiner* — Kathleen S Holwerda
*Assistant Examiner* — Brooke Labranche

(57) ABSTRACT

A device for use within an occluded biological vessel and a method of using same to remove occlusion material from a vessel are provided. The device includes an elongated body configured for delivering extensions arranged around a distal portion thereof into the biological vessel. Each of the extensions includes an array of projections spaced apart to match openings in a biological mesh forming a part of the occlusion material.

12 Claims, 11 Drawing Sheets

(56) References Cited

U.S. PATENT DOCUMENTS

| | | |
|---|---|---|
| 5,003,657 A | 4/1991 | Boiteau et al. |
| 5,009,659 A | 4/1991 | Hamlin et al. |
| 5,129,910 A | 7/1992 | Phan et al. |
| 5,133,733 A | 7/1992 | Rasmussen et al. |
| 5,192,290 A | 3/1993 | Hilal |
| 5,370,653 A | 12/1994 | Cragg |
| 5,421,832 A | 6/1995 | Lefebvre |
| 5,522,825 A | 6/1996 | Kropf et al. |
| 5,702,413 A | 12/1997 | Lafontaine |
| 5,769,960 A | 6/1998 | Nirmel |
| 5,827,304 A | 10/1998 | Hart |
| 5,836,032 A | 11/1998 | Hondo |
| 5,895,400 A | 4/1999 | Abela |
| 5,902,263 A | 5/1999 | Patterson et al. |
| 5,984,965 A | 11/1999 | Knapp et al. |
| 6,027,514 A | 2/2000 | Stine et al. |
| D435,944 S | 1/2001 | Luoma |
| 6,254,571 B1 | 7/2001 | Hart |
| 6,350,271 B1 | 2/2002 | Kurz et al. |
| 6,458,139 B1 | 10/2002 | Palmer et al. |
| 6,692,504 B2 | 2/2004 | Kurz et al. |
| 6,775,873 B2 | 8/2004 | Luoma |
| 7,008,434 B2 | 3/2006 | Kurz et al. |
| D532,978 S | 12/2006 | Robinson |
| 7,416,555 B2 | 8/2008 | Krivoruchko |
| D610,761 S | 2/2010 | Gengler et al. |
| 7,731,731 B2 | 6/2010 | Abela |
| 8,021,379 B2 | 9/2011 | Thompson et al. |
| 8,021,380 B2 | 9/2011 | Thompson et al. |
| 8,034,095 B2 | 10/2011 | Randolph et al. |
| 8,062,307 B2 | 11/2011 | Sepetka et al. |
| D659,918 S | 5/2012 | Zach et al. |
| 8,365,337 B2 | 2/2013 | Tash |
| 8,545,499 B2 | 10/2013 | Lozier et al. |
| 8,784,434 B2 | 7/2014 | Rosenbluth et al. |
| 8,814,892 B2 | 8/2014 | Galdonik et al. |
| 8,852,205 B2 | 10/2014 | Brady et al. |
| 9,113,857 B2 | 8/2015 | Sethi |
| 9,131,988 B2 | 9/2015 | Bagwell et al. |
| 9,138,307 B2 | 9/2015 | Valaie |
| 9,194,114 B2 | 11/2015 | Petry |
| 9,216,034 B2 | 12/2015 | Avneri et al. |
| 9,217,243 B2 | 12/2015 | Gwen |
| 9,220,499 B2 | 12/2015 | Viola |
| 9,717,519 B2 | 8/2017 | Rosenbluth et al. |
| 2001/0016962 A1 | 8/2001 | Moore et al. |
| 2002/0147458 A1 | 10/2002 | Hiblar et al. |
| 2004/0215222 A1 | 10/2004 | Krivoruchko |
| 2005/0216050 A1 | 9/2005 | Sepetka et al. |
| 2006/0184194 A1 | 8/2006 | Pal et al. |
| 2006/0287667 A1 | 12/2006 | Abela |
| 2007/0066991 A1 | 3/2007 | Magnuson |
| 2007/0118165 A1 | 5/2007 | DeMello et al. |
| 2008/0033423 A1 | 2/2008 | Peacock, III |
| 2008/0167678 A1 | 7/2008 | Morsi |
| 2008/0262495 A1 | 10/2008 | Coati et al. |
| 2009/0054805 A1 | 2/2009 | Boyle, Jr. |
| 2009/0112239 A1* | 4/2009 | To .................. A61M 25/1027 606/159 |
| 2010/0249815 A1 | 9/2010 | Jantzen et al. |
| 2011/0144671 A1 | 6/2011 | Piippo Svendsen et al. |
| 2012/0005849 A1 | 1/2012 | Tash |
| 2012/0172656 A1 | 7/2012 | Walters et al. |
| 2014/0135814 A1 | 5/2014 | Sepetka et al. |
| 2014/0309657 A1 | 10/2014 | Ben-Ami |
| 2014/0371782 A1 | 12/2014 | Galdonik et al. |
| 2015/0018859 A1 | 1/2015 | Quick et al. |
| 2015/0119896 A1 | 4/2015 | Krolik et al. |
| 2015/0164630 A1* | 6/2015 | Johnson .................. A61F 2/01 606/200 |
| 2016/0051261 A1 | 2/2016 | Centeno et al. |
| 2016/0221050 A1 | 8/2016 | Beck et al. |
| 2018/0235645 A1 | 8/2018 | Ben-Ami |

FOREIGN PATENT DOCUMENTS

| | | |
|---|---|---|
| CN | 1501825 | 6/2004 |
| CN | 101035474 | 9/2007 |
| CN | 102170833 | 8/2011 |
| CN | 104093369 | 10/2014 |
| DE | 102004040868 | 3/2006 |
| GB | 2459481 | 10/2009 |
| JP | 2003-010193 | 1/2003 |
| JP | 2003-038500 | 2/2003 |
| WO | WO 94/023787 | 10/1994 |
| WO | WO 2005/102184 | 11/2005 |
| WO | WO 2012/110619 | 8/2012 |
| WO | WO 2013/105099 | 7/2013 |
| WO | WO-2013105099 A2 * | 7/2013 |
| WO | WO 2016/120864 | 8/2016 |

OTHER PUBLICATIONS

Official Action dated Oct. 18, 2017 From the US Patent and Trademark Office Re. U.S. Appl. No. 14/315,352. (13 Pages).
Decision of Rejection dated Dec. 12, 2017 From the Japan Patent Office Re. Application No. 2014-551729. (2 Pages).
Communication Under Rule 71(3) EPC dated Dec. 15, 2017 From the European Patent Office Re. Application No. 13735641.6. (37 Pages).
Translation of Decision of Rejection dated Dec. 12, 2017 From the Japan Patent Office Re. Application No. 2014-551729. (4 Pages).
Notification of Office Action dated Jan. 25, 2018 From the State Intellectual Property Office of the People's Republic of China Re. Application No. 201610379472.1 and Its Translation into English. (12 Pages).
Notice of Allowance dated Mar. 2, 2018 From the US Patent and Trademark Office Re. U.S. Appl. No. 14/315,352. (17 pages).
Office Action dated Mar. 7, 2018 From the Israel Patent Office Re. Application No. 233660 and Its Translation Into English. (5 Pages).
Advisory Action Before the Filing of an Appeal Brief dated Mar. 20, 2017 From the US Patent and Trademark Office Re. U.S. Appl. No. 14/315,352. (3 pages).
Communication Pursuant to Article 94(3) EPC dated Mar. 10, 2016 From the European Patent Office Re. Application No. 13735641.6.
Communication Pursuant to Article 94(3) EPC dated Jun. 23, 2017 From the European Patent Office Re. Application No. 13735641.6. (5 Pages).
International Preliminary Report on Patentability dated Jul. 24, 2014 From the International Bureau of WIPO Re. Application No. PCT/IL2013/050049.
International Search Report and the Written Opinion dated Jul. 19, 2013 From the International Searching Authority Re. Application No. PCT/IL2013/050049.
International Search Report and the Written Opinion dated Jul. 29, 2016 From the International Searching Authority Re. Application No. PCT/IL2016/050073.
Invitation to Pay Additional Fees dated May 9, 2016 From the International Searching Authority Re. Application No. PCT/IL2016/050073.
Notice of Reasons for Rejection dated Nov. 15, 2016 From the Japan Patent Office Re. Application No. 2014-551729 and Its Translation Into English. (18 Pages).
Notice of Reasons for Rejection dated May 30, 2017 From the Japan Patent Office Re. Application No. 2014-551729. (5 Pages).
Notification of Office Action and Search Report dated Dec. 4, 2015 From the State Intellectual Property Office of the People's Republic of China Re. Application No. 201380005571.8 and Its Summary of Office Action in English.
Notification of Office Action dated Apr. 1, 2016 From the State Intellectual Property Office of the People's Republic of China Re. Application No. 201380005571.8 and Its Summary in English.
Notification of Office Action dated Jul. 5, 2016 From the State Intellectual Property Office of the People's Republic of China Re. Application No. 201380005571.8.
Official Action dated Feb. 22, 2017 From the US Patent and Trademark Office Re. U.S. Appl. No. 14/315,352. (14 pages).

(56) References Cited

OTHER PUBLICATIONS

Official Action dated Oct. 25, 2016 From the US Patent and Trademark Office Re. U.S. Appl. No. 14/315,352.
Official Action dated Mar. 31, 2017 From the US Patent and Trademark Office Re. U.S. Appl. No. 14/315,352. (11 pages).
Patent Examination Report dated Sep. 7, 2016 From the Australian Government, IP Australia Re. Application No. 2013208660.
Restriction Official Action dated Aug. 8, 2016 From the US Patent and Trademark Office Re. U.S. Appl. No. 14/315,352.
Supplementary European Search Report and the European Search Opinion dated May 11, 2015 From the European Patent Office Re. Application No. 13735641.6.
Translation of Notice of Reasons for Rejection dated May 30, 2017 From the Japan Patent Office Re. Application No. 2014-551729. (11 Pages).
Translation of Notification of Office Action dated Jul. 5, 2016 From the State Intellectual Property Office of the People's Republic of China Re. Application No. 201380005571.8.
Notification of Office Action dated Aug. 14, 2018 From the State Intellectual Property Office of the People's Republic of China Re. Application No. 201610379472.1 and Its Summary in English. (5 Pages).
Examination Report dated Apr. 12, 2017 From the Instituto Mexicano de la Propiedad Industril, Direccion Divisional de Patentes, IMPI Re. Application No. MX/a/2014/008474 and Its Translation Into English. (6 Pages).
Official Action dated Jul. 28, 2017 From the US Patent and Trademark Office Re. U.S. Appl. No. 14/315,352. (14 pages).
Requisition by the Examiner dated Sep. 28, 2018 From the Innovation, Science and Economic Development Canada, Canadian Intellectual Property Office Re. Application No. 2,860,301. (4 Pages).
Supplementary European Search Report and the European Search Opinion dated Aug. 24, 2018 From the European Patent Office Re. Application No. 16742884.6. (9 Pages).
International Preliminary Report on Patentability dated Aug. 10, 2017 From the International Bureau of WIPO Re. Application No. PCT/IL2016/050073. (9 Pages).
Office Action dated Jun. 6, 2018 From the Israel Patent Office Re. Application No. 233660 and Its Translation Into English. (4 Pages).
Advisory Action Before the Filing of an Appeal Brief dated Sep. 12, 2017 From the US Patent and Trademark Office Re. U.S. Appl. No. 14/315,352. (3 pages).
Notification of Office Action dated Feb. 3, 2019 From the State Intellectual Property Office of the People's Republic of China Re. Application No. 201610379472.1 and Its Translation of Office Action Into English. (10 Pages).
Notification of Decision of Rejection dated Jul. 22, 2019 From the State Intellectual Property Office of the People's Republic of China Re. Application No. 201610379472.1. (5 Pages).
Notification of Office Action and Search Report dated Jul. 22, 2019 From the State Intellectual Property Office of the People's Republic of China Re. Application No. 201680019053.5 and a Summary of the Notification of Office Action Into English.(19 Pages).
Translation Dated Aug. 11, 2019 of Notification of Decision of Rejection dated Jul. 22, 2019 From the State Intellectual Property Office of the People's Republic of China Re. Application No. 201610379472.1. (5 Pages).
Notice of Reason for Rejection dated Aug. 30, 2019 From the Japan Patent Office Re. Application No. 2017-540079 and Its Translation Into English. (8 Pages).
Notice of Reason for Rejection dated Jan. 7, 2020 From the Japan Patent Office Re. Application No. 2017-540079 and Its Translation Into English. (6 Pages).
Notification of Office Action and Search Report dated Dec. 20, 2019 From the National Intellectual Property Administration of the People's Republic of China Re. Application No. 201680019053.5 and Its Translation Into English.(19 Pages).
Official Action dated Feb. 14, 2020 From the US Patent and Trademark Office Re. U.S. Appl. No. 15/961,909. (48 pages).
Final Official Action dated May 27, 2020 from the US Patent and Trademark Office Re. U.S. Appl. No. 15/961,909. (11 pages).

\* cited by examiner

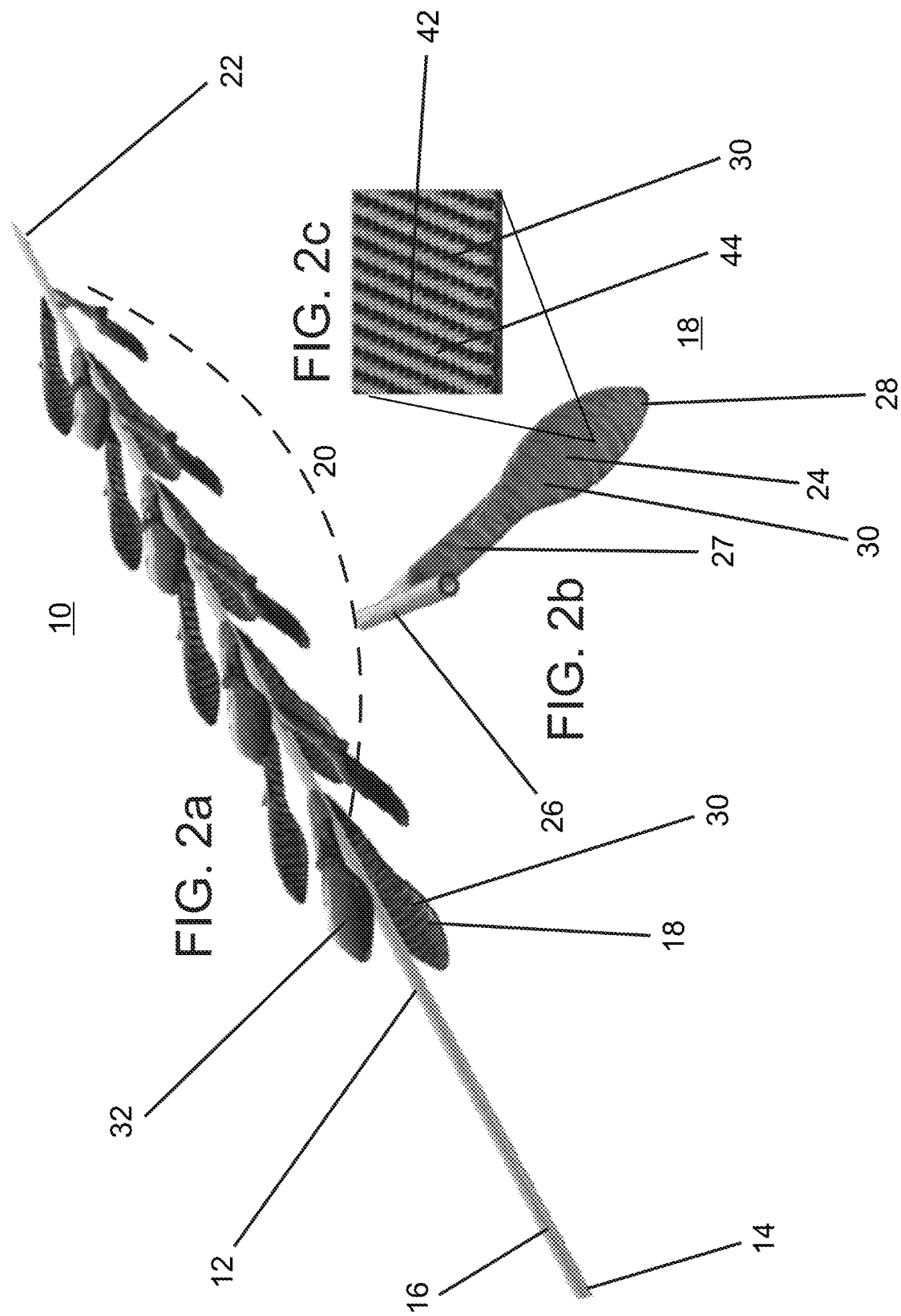

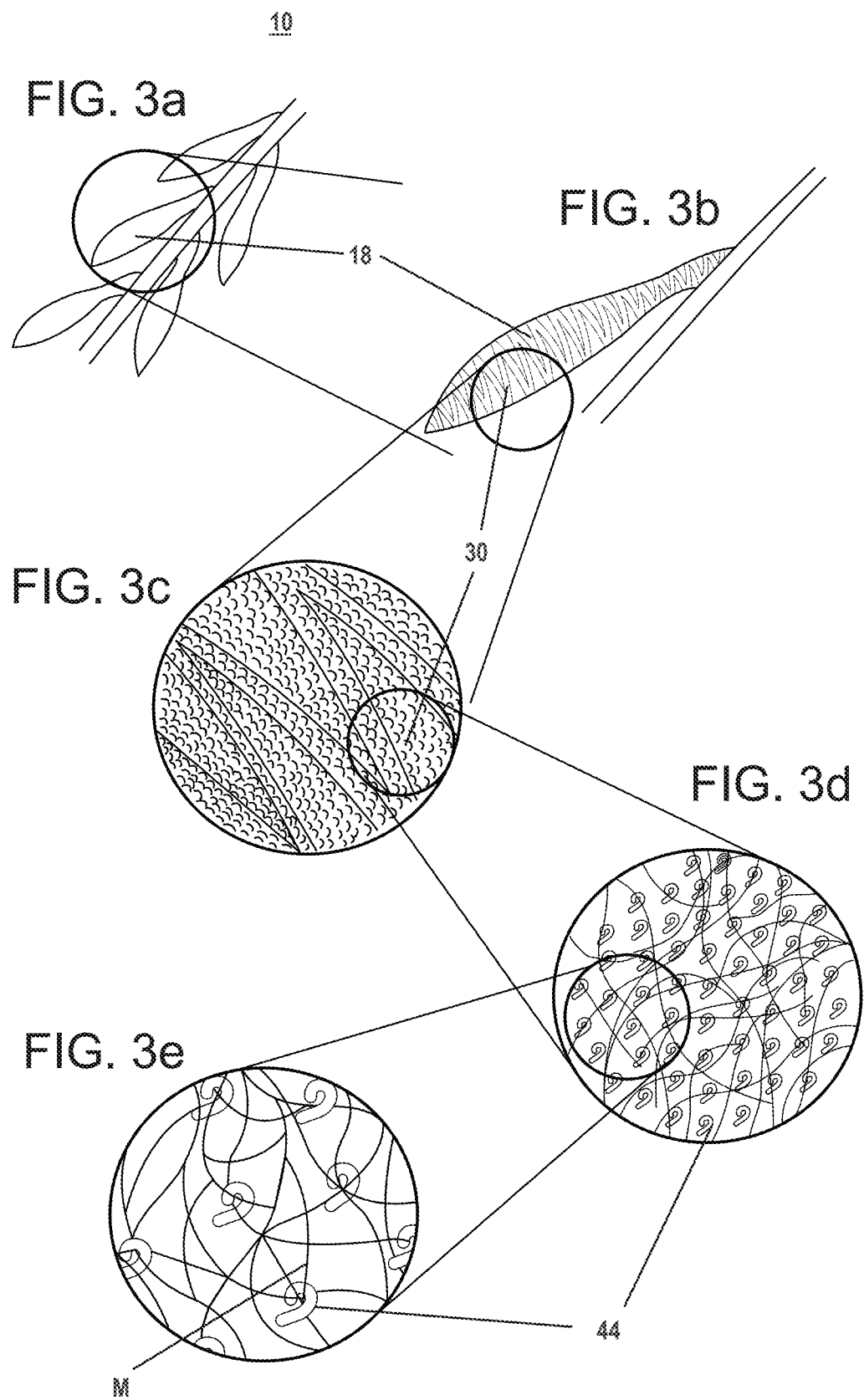

FIG. 4a
FIG. 4b
FIG. 4c
FIG. 4d
FIG. 4e
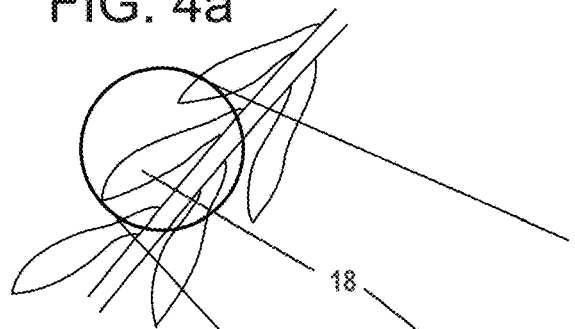
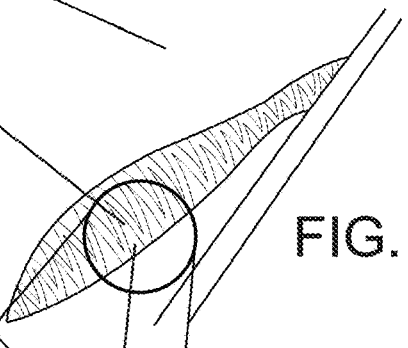
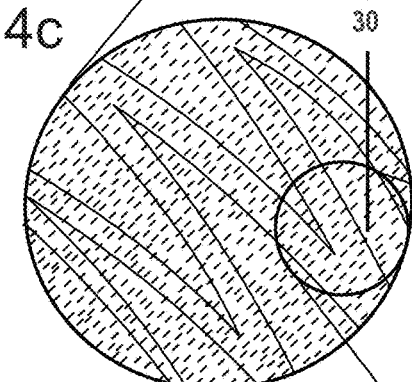
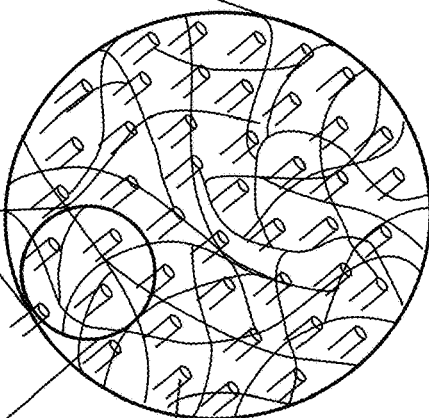
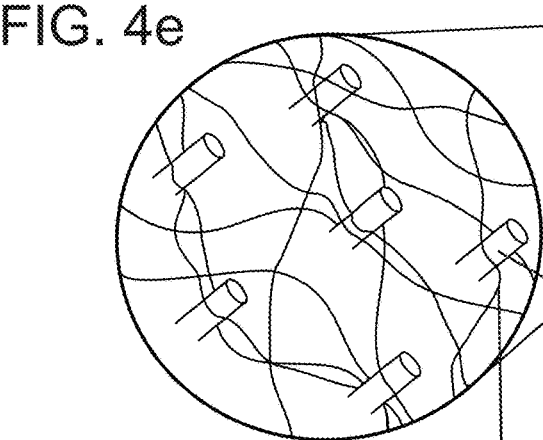

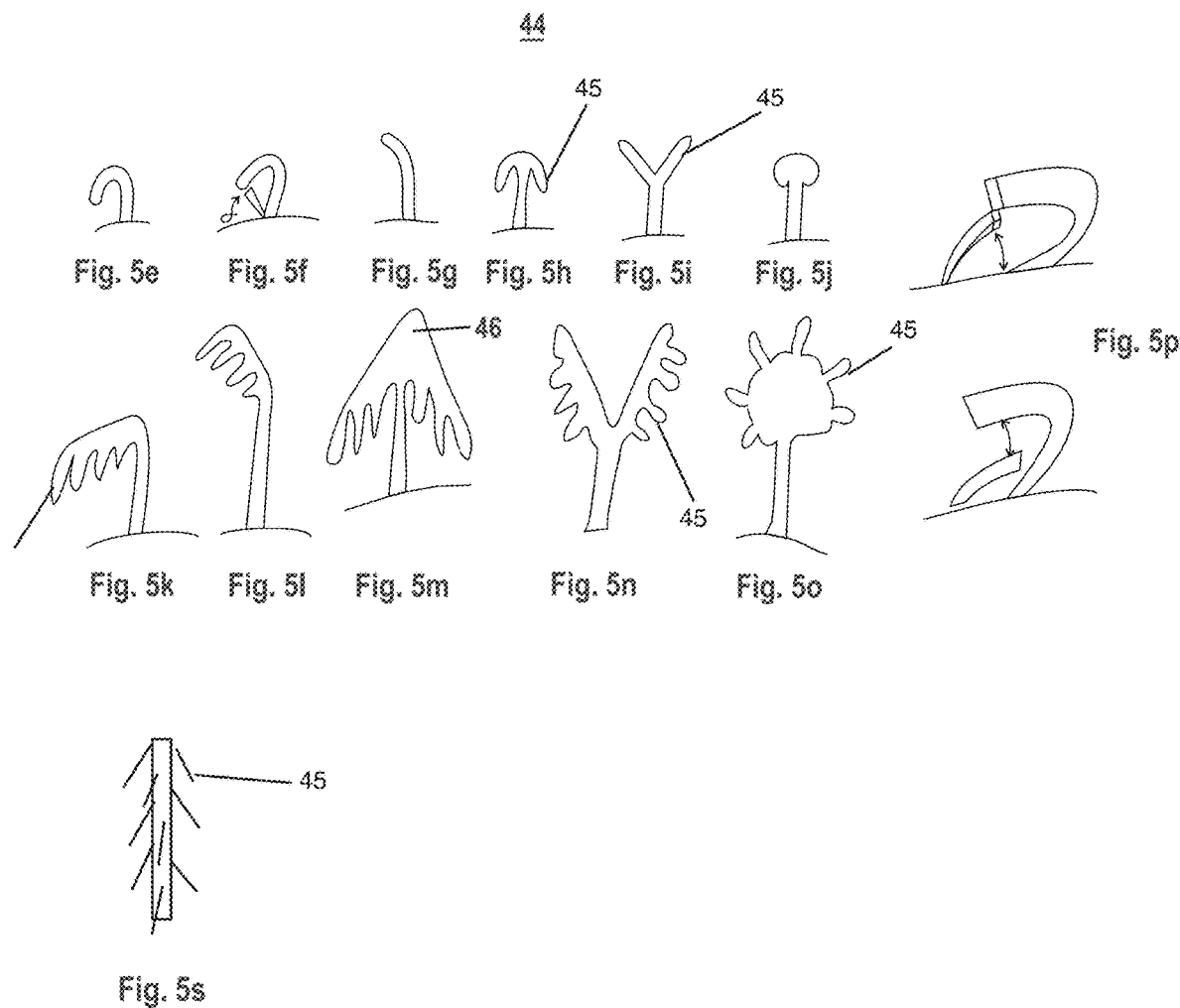

DEVICE AND METHOD FOR REMOVING OCCLUSIONS IN A BIOLOGICAL VESSEL

RELATED APPLICATIONS

This application is a National Phase of PCT Patent Application No. PCT/IL2016/050073 having International filing date of Jan. 25, 2016, which claims the benefit of priority under 35 USC § 119(e) of U.S. Provisional Patent Application No. 62/108,602 filed on Jan. 28, 2015. The contents of the above applications are all incorporated by reference as if fully set forth herein in their entirety.

FIELD AND BACKGROUND OF THE INVENTION

The present invention relates to a device for removing occlusions from a biological vessel. Specific embodiments of the present invention relate to a catheter for dislodging and collecting thrombus material from arteries and in particular brain arteries without compromising the integrity of the thrombus mass.

The rapid and effective treatment of an ischemic stroke is a key factor in minimizing the morbidity and mortality that may otherwise result from this medical emergency. In Ischemic stroke, thrombotic material causes occlusion of the arterial vessels that supply blood to the brain. In general, the removal of these thrombi from an occluded or partly occluded vessel may be attempted by enzymatically disintegrating the thrombus material via agents such as tissue plasminogen activator (tPA) or alteplase (thrombolysis) by administering, or by mechanically removing the thrombus (thrombectomy).

Three general approaches are utilized for mechanically removing thrombus material from a small blood vessel: a distal approach, a medial approach and a proximal approach.

In the distal approach, the distal end of the retrieval device (typically fitted with a distal basket or snare) is passed through the occlusion and positioned at a distal side thereof. The device is then pulled back (in a proximal direction) while the distal end engages the thrombus material. One example of a commercially-available device employing this approach is the Merci retriever, manufactured by Concentric Medical Inc. and described in U.S. Pat. No. 6,663,650.

In the proximal approach, the distal end of the retrieval device (fitted with a grasper or an aspirator) is brought into contact with the proximal side of the thrombus and the thrombus is then pulled proximally through the vasculature and finally removed from the body. One example of a device utilizing the proximal approach is the Penumbra device, manufactured by Penumbra Inc. and disclosed in EP 1799128.

The medial approach is more commonly used and involves opening a stent-like retrieval device inside the thrombus, compressing the thrombus material against the arterial wall and retrieving the device along with the compressed thrombus material.

Although these approaches can be used to at least partially remove thrombus material occluding an artery, such removal can oftentimes be associated with an increased risk of distal emboli and the release of thrombotic debris. In addition, contact of the device with the endovascular wall, especially in the case of stent-like devices can cause trauma to the vascular tissues as well as precipitate vasospasm.

As such, it would be highly advantageous to have an occlusion removal device capable of removing occlusive material from a biological vessel such as a blood vessel while being devoid of the above limitations.

SUMMARY OF THE INVENTION

According to one aspect of the present invention there is provided a device for retrieval of an occlusion in biological vessel comprising an a plurality of extensions arranged around a distal portion of an elongated body, the plurality of extensions each including an array of surface-mounted projections spaced 0.01-500 microns apart.

According to further features in preferred embodiments of the invention described below, at least portion of an extension of the plurality of extension is covered by the array of surface-mounted projections.

According to still further features in the described preferred embodiments the portion is a proximal portion of the extension.

According to still further features in the described preferred embodiments the projections are angled with respect to the surface of an extension.

According to still further features in the described preferred embodiments the angle is selected such that the projections penetrate the occlusion when the plurality of extensions are in contact with the occlusion and pulled proximally through the biological vessel.

According to still further features in the described preferred embodiments the surface-mounted projections are configured with one or more hooks.

According to still further features in the described preferred embodiments the surface-mounted projections taper in diameter from tip to base and optionally include surface mounted protrusions which are mushroom-shaped.

According to still further features in the described preferred embodiments the surface-mounted projections include protrusions along a length thereof.

According to still further features in the described preferred embodiments the extensions are capable of folding against the elongated body when advanced distally through the occlusion in the biological vessel.

According to still further features in the described preferred embodiments the extensions expand radially outward when the device is positioned within the occlusion in the biological vessel and pulled in a proximal direction.

According to still further features in the described preferred embodiments the extensions are leaf-like in shape.

According to still further features in the described preferred embodiments an internal surface of a portion of the extensions is concave.

According to still further features in the described preferred embodiments an internal surface of a portion of the extensions is textured.

According to still further features in the described preferred embodiments the extensions are arranged as pairs along the distal portion.

According to still further features in the described preferred embodiments each pair of the extensions is connected to the elongated body via a swivel.

According to still further features in the described preferred embodiments the extensions are composed of a first material and further wherein the projections are composed of a second material (or the same material).

According to still further features in the described preferred embodiments the first material is softer than the second material.

According to still further features in the described preferred embodiments the extensions include an inward curving distal tip.

According to still further features in the described preferred embodiments the occlusion is a thrombus.

According to still further features in the described preferred embodiments the projections are 1-50 microns in length.

According to another aspect of the present invention there is provided a device for retrieval of an occlusion in biological vessel comprising an a plurality of extensions arranged around a distal portion of an elongated body, the plurality of extensions each including an array of surface-mounted projections, wherein a diameter of a tip of each projection is 100 microns or less.

According to another aspect of the present invention there is provided a method of retrieving a thrombus from a blood vessel, the method comprising (a) positioning in the blood vessel the device described herein; and (b) advancing the distal portion of the device into a thrombus material; and (c) pulling the device proximally to thereby penetrate, dislodge and collect the thrombus material.

The present invention successfully addresses the shortcomings of the presently known configurations by providing a device for effectively and non-traumatically retrieving an occlusion such as a thrombus from a biological vessel such as an artery.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-c illustrate one embodiment of the present device (FIG. 2a), a single extension thereof (FIG. 2b) and a magnified view of an inner surface of the extension (FIG. 2c).

FIGS. 3a-c schematically illustrate a portion of the present device (FIG. 3a) showing an isolated extension (FIG. 3b) and a magnified view of the inner surface of the extension showing the projections (FIG. 3c).

FIGS. 3d-e are successive magnified views of the hook-like projections of FIG. 3c showing engagement with the biological mesh.

FIGS. 4a-c schematically illustrate a portion of the present device (FIG. 4a) showing an isolated extension (FIG. 4b) and a magnified view of the inner surface of the extension showing the projections (FIG. 4c).

FIGS. 4d-e are successive magnified views of the cylindrical (rod-like) projections of FIG. 4c showing engagement with the biological mesh.

DESCRIPTION OF THE PREFERRED EMBODIMENTS

Figure 1A:
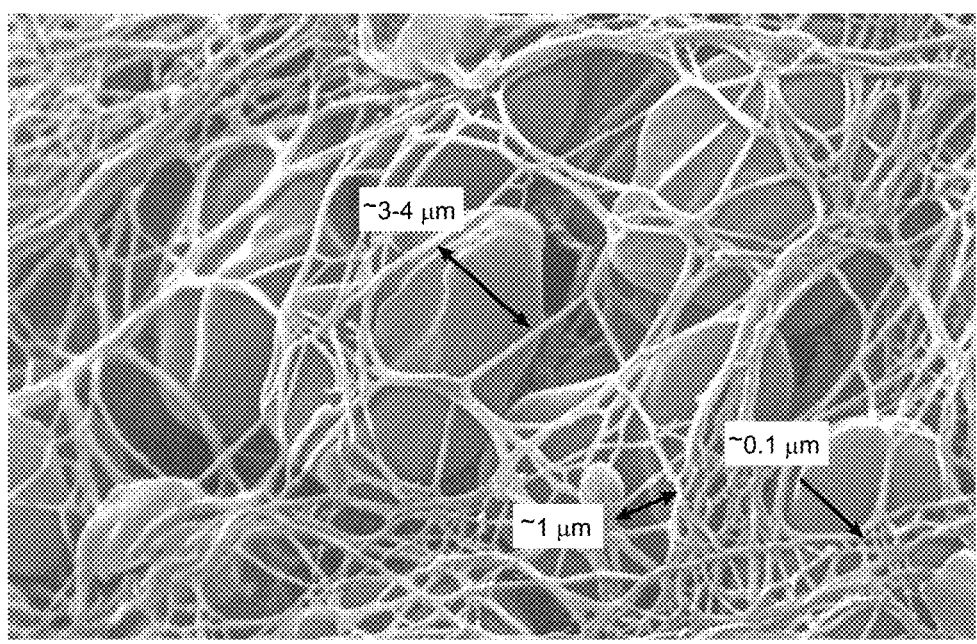
FIGS. 1a-b illustrate a thrombus (FIG. 1a) and the fibrin mesh component (FIG. 1b) thereof.

The present invention is of a device which can be used to retrieve occlusions from a biological vessel. The present invention is particularly useful for unblocking occluded arteries in various parts of the body including the brain.

The principles and operation of the present invention may be better understood with reference to the drawings and accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

In order to effectively clear an occlusion from an artery, thrombus material must be effectively penetrated, engaged/anchored, dislodged and retrieved from the vessel without releasing particles into circulation and while creating minimal irritation/damage to the vessel wall.

Catheters having clot retrieval heads designed for maximizing clot engagement and retrieval are known in the art (e.g. U.S. Pat. Nos. 5,895,400, 7,731,731, 5,702,413, 5,827,304, 6,350,271, 6,692,504 or 7,008,434). However, such catheters may be less effective for retrieving thrombus material or minimizing damage to the vessel wall since there is oftentimes a tradeoff between effective thrombus engagement and a need to minimize damage to, and vasospasm of the arterial walls.

In a previously filed patent application, the present inventor described a catheter that is effective at penetrating, engaging, dislodging and retrieving thrombus material while minimizing damage to the vessel wall. This catheter includes relatively soft leaf-like structures attached to a relatively rigid stem which is in turn mounted on an elongated body. The surface of the leaf-like structures is covered with macro and micro structures for enhancing engagement between the 'leaf' surface and the thrombus.

While experimenting with several device prototypes, the present inventor realized that engagement between the catheter 'leaves' (herein generally referred to as "extension") and occlusive material can be further enhanced by utilizing surface projections designed for specifically engaging a repeating structure forming a part of the occlusive material.

Thus, according to one aspect of the present invention there is provided a device for removing (clearing and optionally retrieving) occlusions in a biological vessel. As used herein, the phrase "biological vessel" refers to any vessel capable of supporting flow of a biological material. The vessel can be a natural vessel or a synthetic vessel implanted in a body. Examples of vessels include blood vessels such as veins or arteries, lymphatic vessels, urinary system vessels such as the urethra or ureters, seminal vessels, saliva ducts, bile ducts, synthetic vessels graft, such as arteriovenous (AV) graft and more. Occlusions are any flow limiting blockages in the vessel which are caused by local buildup of atherosclerotic material, atherosclerotic emboli, migrating blood clots, biological stones, foreign bodies or the like.

The device includes an elongated body for delivering a plurality of extensions arranged around a distal portion of the elongated body into the biological vessel. The device can be configured as a catheter for use with a guidewire in clearing thrombus material from a blood vessel. When configured as a catheter, the elongated body can include a longitudinal lumen sized for accepting a guidewire (e.g. 0.014", 0.018" or 0.035" or other guidewires). The lumen can be configured for use with over-the-wire, or rapid exchange systems.

The device can also be delivered within a hollow catheter/delivery tube (guiding catheter). In such cases, the catheter/delivery tube is positioned using a guidewire which is then removed to allow positioning of the present device.

The elongated body can be 10 to 200 cm in length with a width/diameter of 0.05-50 mm when in closed configuration (suitable for delivery within a 0.1-30 F sheath. The elongated body is preferably shaped as shaft (rod or tube) and is fabricated from any bio-compatible material, including, for example, alloys such as stainless steel, Nitinol or polymers such as Polyimide (PI), Polyether Block Amide (PEBA)-Pebax. The elongated body is preferably axially rigid in order to facilitate lodging of the distal portion (carrying the extensions) into the occlusion and yet flexible enough to facilitate navigation through torturous vessels while ensuring safety (e.g. blood vessels in the brain). Rigidity of the elongated body (catheter) is same range as catheters commonly used for navigating biological vessels such as blood vessels.

The distal portion of the elongated body includes extensions that project radially outward, preferably at an angle (of 0-90 degrees) towards the proximal end of the elongated body. The extensions can be of any shape (rectangle, triangle, oval, polyangular-shaped, spiral, or a combination of several shapes including simple or complex shapes with fractal characteristics) and of any profile (round, oval, rectangle). The extensions can be directly connected to the elongated device body, or connected thereto through a joint element (e.g. stem).

The axial rigidity of the stem portion of the extension can be preferably anywhere from 0.1-100 grams (e.g. 10-90, 20-80, 30-70, 40-60) or more depending on the occlusion location, occlusion type and size, extension structure and material the stem is constructed from. The axial rigidity of the extension can be anywhere from 0.0-50 grams (e.g. 5-40, 10-30, 20-25) or more depending on the occlusion location, occlusion type and size and the structure and material the extension is constructed from.

The extensions and optionally stems are preferably elastically deformable and fabricated from elastomeric material such as thermoplastic elastomers (TPEs), silicone, other plastics or metal alloys such as Nitinol. Elasticity is selected such that when the device is advanced distally into an occlusion (thrombus) within the biological vessel, the extensions fold against the elongated body due to the forces exerted by the occlusion/thrombus mass. This enables the extensions to penetrate an occlusion (e.g. thrombus) in the vessel without crossing or deploying distally outside to the thrombus mass and lodge therein. When the device is pulled in a proximal direction, the extensions deploy outward (to the angle set by the stems or the vessel wall limitation) due to the drag forces exerted by the occlusion (thrombus) mass thereby enabling the device to engage/anchor to the occlusion material, dislodge it from the vessel wall and remove it.

Typical dimensions for the extensions can be 0.2-30 mm in length, 0.05-20 mm in width, 0.03-3 mm in thickness, with a single side surface area of 0.01-600 $mm^2$.

The stems portions can be 0.1-20 mm in length, 0.02-20 mm in width, 0.03-3 mm in thickness.

Any number of extensions can be carried on the elongated body depending on the biological vessel, occlusion size and type and function of the device. A typical number of extensions can range from 1-20 or more. The extensions can be carried as pair, triplets etc on a fixed or swiveling joint.

The internal surface (facing towards the elongated body) of the extensions is preferably concave in order to increase the surface area thereof and the drag/resistance force exerted on the internal surface by the thrombus mass. Such a concave configuration also increases the ability of the extensions to collect (scoop) the occlusion material. The exterior surface of the extensions is preferably convex to facilitate delivery within the vessel and lodging of the projections into the occlusion while folded in a "close configuration" (arrow like) due to the drag forces exerted on the extensions by the occlusion material when the extensions are advanced into the occlusion. Although such a configuration is preferred, internal and external surfaces having alternative contours (e.g. flat on both sides) are also envisaged herein.

Each extension can also fold in half lengthwise to further improve penetration into the occlusion material. Such folding can occur during use, in accordance with the mechanical forces exerted upon the extensions by the occlusion material and the vessel wall.

The distal portion (tip) of the extension is preferably curved inward in order to minimize trauma/damage to the vessel when the device is navigated within the blood vessels. To further decrease trauma and irritation to the vessel wall, the tips can be fabricated from a very soft material (softer than the rest of the leaf-like structure).

The inward curving tips can also facilitate hooking of the projections into the occlusion material.

The inner (and optionally outer) surface of the extensions includes surface mounted projections arranged as an array of specific size and distribution in order to enable the extensions to engage a repeating structure on the surface of the occlusion.

The outer surface of the extensions (and optionally elongated body) can be textured with numerous rounded bumps (several microns to several hundred microns in height and diameter) or hills and valleys or coated with a low friction coating (e.g. Parylene, polydimethylsiloxane) in order to minimize the contact area and overall friction between the outer surface of the extensions and the vessel wall. This enables the device to slide better against the vessel wall when navigated through the torturous cerebral vasculature.

Figure 1B:
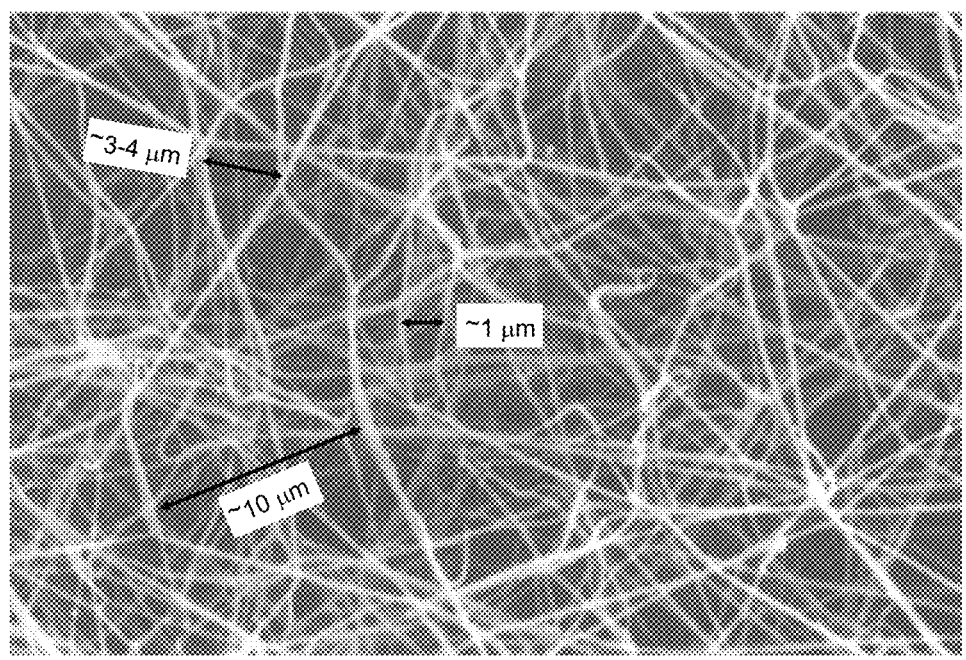

In the case of a thrombus, this repeating structure is the fibrin mesh component of the thrombus. A blood clot or thrombus (FIG. 1a) includes a fibrin mesh (FIG. 1b) with entrapped blood cells and platelets.

The fibrin mesh serves as the thrombus "skeleton structure" and provides stability as well as imparting a gel-like property to the blood clot. The fibrin fibers are organized in a 3D mesh configuration with an average pore size of 0.1-50 microns. The fiber diameter is between 50-500 nanometer. An experiment conducted by Liu et al. (The mechanical properties of single fibrin fibers; J Thromb Haemost. May 2010) showed that the fibrin fiber can stretch to a length 2.5-3.3 times the relaxed length before rupturing.

Thus, in order to maximize engagement between an extension and the fibrin mesh, the distribution of the projections on the surface of the extension and the shape and size of each projection must be designed to enable the following:

(i) penetration without "disturbing" the thrombus structure of at least a tip of the projection through an opening in the fibrin mesh;

(ii) attachment of at least the tip of the projection to the mesh fiber following penetration; and/or (iii) maximizing contact area between the extension and the occlusion at the nano scale to harness intermolecular forces such as Van der Waals forces.

In order to enable the above, the projections are preferably arranged as an array of at least 100 projections (anywhere from several hundred to several millions projections per cm$^2$ of surface area) spaced apart by 0.01-500 microns (at the surface-contacting base). The array can be of any shape (circular, triangular, square etc) and can include one or more types (shapes) of projections. A projection can be 0.001-5,000 microns in height (length from base to tip) with a uniform or varying diameter or width throughout its length. Each projection can be angled at 90 degrees or less with respect to the surface of the extension in the direction of the base, tip or sides of the extension. The array can include projections that are identical or different with respect to degree of angulation and/or direction of angulation.

The projections can be simple (e.g. cylindrical rod) or complex (e.g. 'Christmas tree' or 'mushroom') in shape and can include surface coating (composition for enhancing attachment to occlusion) or surface texturing (e.g. "fractal-like" texturing, e.g. gecko-like texturing).

The unique configuration of the extensions and projections of the present device provides several advantages in clearing occlusions in a biological vessel.

(i) Delivery and penetration of occlusion material—when the present device is advanced in a distal direction the contour of the external surface and elasticity of the extensions enable folding thereof which reduces the profile of the device and also streamlines the outer surface of the folded extension. This enhances delivery and minimizes disruption of the occlusion (which can lead to release of embolic particles).

(ii) Engagement/anchoring of occlusion material—when the present device is pulled in a proximal direction, drag forces are applied to the inner surfaces of the extensions and causes them to open. This increases the cross sectional area of the device and its surface interaction with the occlusion and exposes the occlusion material to the array of surface mounted projections which penetrate and attach to the repeating structure forming a part of the occlusive material. In addition, exposure of the inward curving tips to the occlusion material, increases penetration and lodging of the extensions in the occlusion material (thereby forcing more projections into the occlusion material). The stem portion prevents the projections from flipping over thereby ensuring that a pulling force at the handle/proximal part of the device is efficiently converted to engagement/anchoring force. In cases where the drag forces on the extensions is above a certain threshold, the extensions will flip over in order to prevent injury or retention of the device. However, even in cases where the extensions flip over, the projections and protrusions will ensure that the thrombus remains attached to the extension.

(iii) Dislodgement of occlusion material—the pulling force at the handle/proximal part of the catheter is also efficiently converted to a proximal movement of the catheter-occlusion complex. The extensions can be designed such that the forces applied thereby are matched to the type and location of occlusion. The forces applied by the extensions on the occlusion are a function of the occlusion material, size and the properties of the occlusion and the vessel surrounding it, thus minimizing unnecessary force and distortion of the thrombus natural configuration. In addition, cooperative engagement between numerous projections and occlusion material further enhances attachment of extensions to the occlusion.

(iv) Removal of occlusion—the increased surface area, and the multiple engagement areas (array of projections), as well as the unique scoop-like shape of the internal surface of the extensions facilitate collection of dislodged material. The occlusion material is trapped within the extension by the projections creating a catheter-thrombus complex that can be removed as one piece.

The present invention is described in greater detail hereinbelow with reference to FIGS. 2a-5s.

Referring now to the drawings, FIG. 2a illustrates a thrombus retrieval device which is referred to herein as device 10.

Device 10 is configured suitable for entering, engaging/anchoring, dislodging and collecting thrombus material from a blood vessel and in particular small blood vessels of the brain, as well as other blood vessels.

Device 10 includes an elongated body 12 having a handle 14 (user engaged portion) at proximal end 16 and extensions 18 (16 shown) attached to a distal portion 20. Elongated body 12 includes a nose cone 22 for facilitating non-traumatic delivery into a vessel and also allows penetration into the occlusion/thrombus.

Extensions 18 are preferably arranged singly or as pairs (arrangements including 3, 4, 5, 6 or more projections are also possible) around distal portion 20, with each single or pair rotated 0-180 degrees from an adjacent single pair.

FIG. 2b illustrates an isolated extension 18 showing extension body 24 attached to a connector 26 via stem 27. Connector 26 can be glued or mechanically coupled to elongated body 12. Preferably, connector 26 is a cylindrical connector which is fitted around elongated body 12 and fixedly attached thereto or allowed to swivel. Extension 18 can alternatively be connected directly to elongated body 12 without use of a connector.

Device 10 can further include a web like element interposed between extensions 18. Such an element can supplement the ability of device 10 to capture/harvest dislodged occlusion material.

Extension body 24 is leaf-shaped and includes an inward curving tip 28 for minimizing damage or irritation to the vessel wall when device 10 is pushed and pulled within the vessel. Inward curving tip 28 also functions to facilitate lodging of extensions 18 into occlusion material (e.g. thrombus material) when device 10 is pulled in a proximal direction.

As is shown in FIG. 2b, inner surface 30 of extension body 24 is concave to increase surface contact area and drag forces when the device is pulled proximally and to scoop the occlusion material dislodged from the vessel wall.

Inner surface 30 can also be textured (e.g. micro/nano structures, not shown) to enhance surface contact area at the macro/micro/molecular level.

Outer surface 32 of extension body 24 (FIG. 2a) is convex to decrease drag forces when extensions 18 penetrate the thrombus mass. The convex outer surface 32 also allows extensions 18 to fold into a compact streamlined configuration for delivery into the vessel and occlusion. Additional hydrodynamic streamlining of extensions 18 may be effected by providing outer surface 32 with one or more bumps/protrusions/channels etc.

Extensions 18 can be fabricated from a single material or from two or more materials. For example, in the embodiment shown in FIG. 2a, extensions can be molded from a single material (e.g. silicone, teflon, nylon and any other elastomer, metal alloys such as Nitinol or elastomer with combination with metal alloys such as Nitinol), with the differential rigidity provided by varying the durometer of the material (e.g. molding stem 27 and optionally connector 26 from a different structure, a silicone having a higher Shore A value or increased thickness, or by using a different material or a combination of different materials).

FIG. 2c is a magnification of inner surface 30 of extension body 24 (of the region circled in FIG. 2b) showing array 42 including a plurality of projections 44. Array 42 can be attached to a smooth or textured surface (such as the textured surface described above).

Projections 44 can be fabricated from the same material as the extensions 18, or from a different material. Examples of suitable materials for construction of extension 18 include silicone, teflon, nylon and any other elastomer, metal alloys such as Nitinol or elastomer with combination with metal alloys such as Nitinol. The projections can be attached to the surface, co formed therewith, or deposited thereupon using well known plasma deposition approaches.

FIGS. 3a-c illustrate a portion of device 10, an extension 18 thereof and a magnified view of inner surface 30 of extension 18 showing projections. FIGS. 3d-e are magnified views illustrating engagement between hook-like projections 44 and a fibrin mesh (M) component of a thrombus.

Hook-like projections 44 can be 0.3-3.0 microns long, 0.2-1 microns in diameter, with a hook angle of 30-90 degrees relatively to the surface. The radius of curvature of the hook portion can be 0.2-1.0 microns.

When configured as hooks, projections 44 are designed to penetrate through the openings in the fibrin mesh and hook onto the fibrin fiber when device 10 is retracted. Cooperative hooking of several projections 44 would substantially increase the engagement force between extension 18 and the thrombus mass thereby enabling retrieval of the thrombus mass when device 10 is retracted out of the vasculature.

FIGS. 4a-c illustrate a portion of device 10, an extension 18 thereof and a magnified view of inner surface 30 of extension 18 showing cylindrical (rod-like) projections 44. FIGS. 4d-e are magnified views illustrating engagement between cylindrical projections 44 and a fibrin mesh component of a thrombus. Cylindrical projections 44 have a size similar to that of hook-like projections described above.

Cylindrical projections 44 are designed to penetrate through the openings in the fibrin mesh and provide a large region of perpendicular contact between projections 44 and the fibrin fibers. Cooperative penetrations of several projections 44 through several openings in the fibrin mesh substantially increase the surface contact area and the engagement force between extension 18 and the thrombus mass thereby enabling retrieval of the thrombus mass when device 10 is retracted out of the vasculature.

Cylindrical projections 44 preferably include surface texturing or protrusions 45 (e.g. downward-pointing protrusions, see FIGS. 5b, d, k, m and n) which engage the fibrin fiber when device 10 is retracted.

Figure 5A:
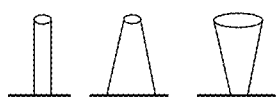
FIGS. 5a-s illustrate various embodiments of the surface-mounted protrusions of the device of the present invention.
Figure 5B:
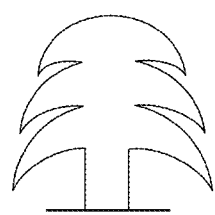
Figure 5C:
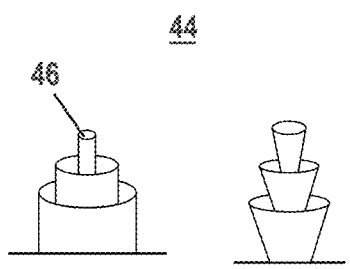
Figure 5D:
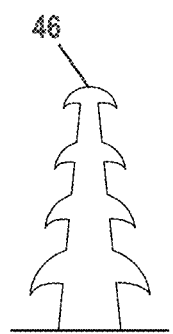
Figures 5Q, 5R:
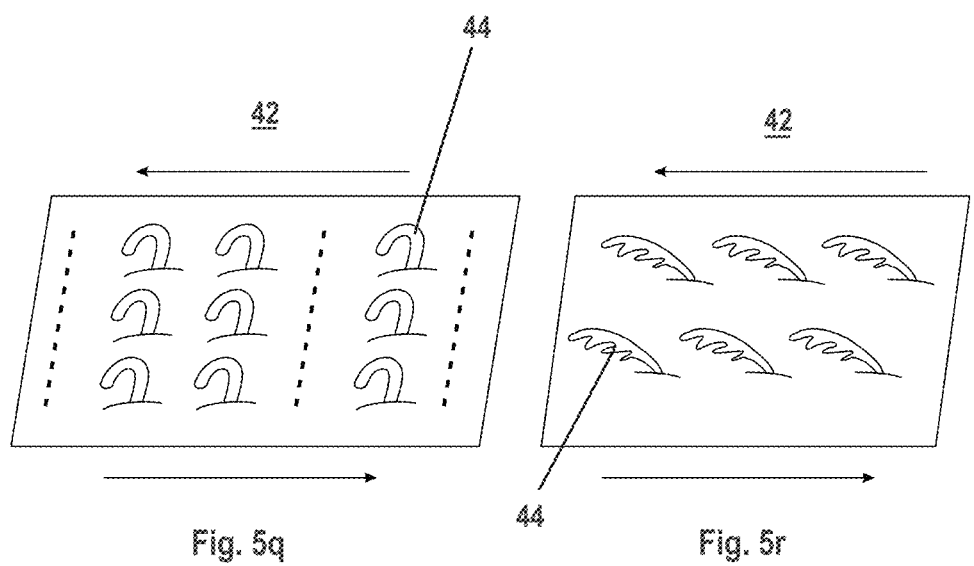

FIGS. 5a-s illustrate several embodiments of projections 44. Each embodiment is characterized by a specific configuration which facilitates engagement between projection 44 and the fibrin mesh. For example, projection 44 can be configured with side or downward pointing side protrusions 45 (FIGS. 5b, d and 5k-n), a bulbous or mushroom-shaped tip (FIG. 5j), a branching tip (FIG. 5o), a loop-gate (e.g. 'carabiner') lock (FIG. 5p), an upright or inverted tree-like structure (FIGS. 5b, d and 5c respectively), sideward or downward projecting hair-like structures (FIG. 5s), comb-like structure, scales, and the like. A projection 44 can include one or more of these structures arranged along a length thereof.

These structures facilitate engagement between projections 44 and the fibrin mesh component of a thrombus by collectively penetrating openings of the mesh and engaging mesh fibers.

It will be appreciated that not every projection 44 will engage the fibrin mesh since an orientation of array 42 with respect to the fibrin mesh of the thrombus cannot be controlled or predetermined. However, an array 42 which includes several thousand projections 44 or more, will likely engage the fibrin mesh of a thrombus through at least several hundred projections 44 thus substantially increasing the 'adhesive' force between each extension and the thrombus.

In addition, in order to maximize engagement to a fibrin mesh of unknown orientation, the present device can include extensions 18 on which projections 44 are oriented in different directions, or include extensions having tips 46 (e.g. FIG. 5c-d, m) that guide projections 44 into the openings of the fibrin mesh.

This structural asymmetry of an array 42 enables engagement with the mesh through one or more directions and thus can maximize engagement when the specific orientation of the fibrin mesh with respect to an extension 18 is unknown. In addition, since device 10 typically includes a number of extensions 18, having various configurations of array 42 on several extensions 18 again maximizes the statistical probability of mesh penetration by projections 44.

As is mentioned hereinabove, the embodiment of device 10 of FIG. 2a is configured for use in clearing obstructions in a blood vessel, preferably a small brain artery that is 0.5-7 millimeter in diameter. As such, elongated body 12 of device 10 is preferably 10-200 centimeter in length, 0.5-7 millimeter in diameter when in closed configuration, while extensions 18 are preferably 0.2-30 mm in length. The length of extension body 24 is preferably 0.1-30 mm and the width (at the widest thereof) is preferably 0.05-20 mm. Stem portion 27 is preferably 0.1-20 mm in length and 0.02-20 mm in width (at the base).

Extensions 18 can be folded against elongated body 12 to an overall diameter of 0.5-7 millimeter. When folded, device 10 can be packed into a 1.5-22 F sheath for delivery through an access site. Once pushed out of the sheath, extensions 18 are folded outward to a position constrained by stem portion 27 (or vessel wall) while distal portion 20 is advanced to the site of occlusion. Since extension body 24 includes a non-traumatic tip 28 (fabricated from a soft material such as silicone), advancing device 10 in the distal direction (towards occlusion) does not traumatize or irritate the vessel wall. Once in position, pulling on handle/proximal catheter part 14 deploys extensions 18 to an angle limited by stem portions 27 or the vessel wall. Such an angle can be 90 degrees or less, preferably 30-45 degrees. At such an angle, tip 28 is angled inward to eliminate trauma and irritation to vessel wall.

The flexible nature of extensions 18 permits the device to automatically adapt to the inner diameter of the blood vessel in which device 10 is situated.

Stem portion 27 and/or extension body 24 can also be configured such that when folded against elongated body 12, the longitudinal axis of extension body 24 is angled with respect to the longitudinal axis of elongated body 12. This increases the exposure of inner surface 30 to the biological fluid in the vessel and to the occlusion material and increases drag and likelihood of deployment when device 10 is pulled in a proximal direction.

A roll angle can also be added such that each extension 18 has an "angle of attack" relative to the movement vector (angle range 0-90 degrees) i.e. to the anterior edge of extension body 24 relative to movement of device 10. The angle of attack in the forward motion (when device 10 is pushed towards occlusion) will have hydrodynamic features and a curve design that will ensure an ability to optimally penetrate and minimally disrupt the thrombus structure. When device 10 is pulled proximally, the angle of attack (which is the opposite edge) can be shaped in a more acute curve structure in order to allow optimal drag forces of the thrombus on each extension 18 thereby ensuring opening thereof. Extensions 18 can also be configured to spiral around elongated body 12.

The size shape and properties of extensions 18 and of projections 44 can be configured according to the biological vessel and occlusion properties. For example, there are two type of thrombus occlusions, a 'red' thrombus (fresh, acute whole blood thrombus) and a 'white' thrombus (relatively chronic embedded with cholesterol and calcium). Extensions 18 of device 10 as well as projections 44 can be configured with rigidity properties that match the viscosity ranges of the thrombus.

When configured as a catheter, device 10 includes a lumen for accepting a guidewire for guiding device 10 to a target occlusion within a vessel. The lumen can traverse the entire length of elongated body 12 (when use with an over-the-wire system) to an guidewire inlet opening in a proximal end of elongated body or alternatively, lumen can traverse a portion thereof (when used with a rapid exchange system) to a guidewire inlet opening at a side wall along a length of elongated body 12.

The lumen can also include one or more holes or other opening along a portion of elongated body proximal to extensions 18. Such holes can be in fluid communication with an opening at distal end and would thus enable blood to flow around the occlusion mass once extensions 18 penetrate the occlusion and the distal end crosses the occlusion and is positioned at its distal side.

This will allow reperfusion of the ischemic brain tissue located distally to the occlusion site. The relatively low flow of blood (through the catheter) provides controlled low flow, low pressure reperfusion to the Penumbra brain tissue which is at a metabolic "shutdown" state and thus might be vulnerable to high pressure systolic blood flow. This will prepare the tissue for restoration of full flow following removal of the thrombus.

In cases where delivery is effected through a catheter or guide tube (guiding catheter), delivery and navigation of device 10 can be effected without a guidewire. In any case, a handle 14 or proximal portion of elongated body 12 can be used to guide device 10 (whether over a wire or not) through the vessel and position distal portion 20 at a site of occlusion.

Device 10 can also include radio-opaque markers (e.g. gold, platinum, iridium or combined with the polymer itself or other radio-opaque markers) mounted on the distal end of elongated body 12 (at distal end).

The markers can be mounted on ends of extensions 18 (e.g. at tips 28). When distal portion 20 is positioned outside of the occlusion, extensions 18 extend out and thus when visualized (fluoroscopy) the markers are a predetermined distance apart (e.g. several millimeters). When distal portion 20 is positioned inside an occlusion, extensions 18 fold against elongated body 12 and thus when visualized (fluoroscopy) the distance between the markers is reduced.

Alternatively, one of the markers can be mounted on a foldable wire (e.g. Nitinol, platinum, other metal alloy or polymer wires) extending radially outward from elongated body 12 while a second marker can be attached to elongated body 12. When distal portion 20 is positioned inside an occlusion, the marker wire is folded against elongated body 12 and brought into proximity to the second marker and optionally a third marker. The distance between the markers can be visualized (fluoroscopy) to determine the extent of folding of the extension.

Marker material (e.g. iridium or platinum) can also be included in the material used to fabricate extensions 18 in order to facilitate identification thereof by a surgeon.

In any case, the markers assist the clinician in determining the correct placement of device 10 within a blood vessel and indicate when distal portion 20 enters an occlusion and extensions 18 are lodged therein.

In order to increase the ability of extension 18 to collect occlusion material, inner surface 30 and/or projections 44 can be coated with a substance that can bind the occlusion material. For example, in the case of a thrombus occlusion, inner surface 30 and/or projections 44 can be coated with fibrin or fibrin derivatives.

Device 10 can be used to clear a thrombus from an artery as follows. A guide catheter or guidewire is advanced from an access site (e.g. in a femoral artery) to the carotid artery under angiography. Device 10 is then inserted over-the-wire or through the guide catheter and navigated to the site of the thrombus. The surgeon then advances the distal end of device 10 into the thrombus until the distal end of device 10 reaches the distal end of the thrombus (as visualized via the radio-opaque markers described above). The surgeon then applies a gentle pulling force on device 10 to open extensions 18 and lodge and engage/anchor them within the thrombus. The device is then pulled along with the trapped thrombus.

Device 10 of the present invention can also be configured for use in clearing any type of occlusion from any biological vessels.

In order to enable such functionality, the present device would be designed with surface projections that match the specific architecture of the occlusion.

Prior art devices which utilize macrostructures (e.g. hooks, bristles) to pierce through and engage the thrombus are more likely to cause embolic events since piercing through the thrombus mass can lead to thrombus disintegration.

The present device encapsulates the thrombus and externally engages it through numerous points of contact using texture-specific micro and nano structures positioned on the surface of leaf-like extensions.

Thus, with the present device, engagement of the thrombus mass does not compromise the integrity of the thrombus and use thereof may not require additional use of embolic protection or entrapment devices such as aspirators and traps which complicate and lengthen the procedure and can lead to serious complications such as vessel injury.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Additive Manufacturing of The Present Device

Several configurations of the present device were designed using CAD software (SolidWorks™) and additive manufacturing (also known as 3D printing) approaches were tested for the ability to 'print' the entire device.

Since the projections and protrusions of the present device are micrometric or nanometric in scale, a 3D printing approach capable of such resolution was sought.

Several devices on the market are capable of 3D printing silicone or another suitable polymer at a resolution of 100 nanometers including devices by WACKER CHEMIE and Ingenieure GmbH; Fripp Design Research; NanoScribe, Old World Labs and more.

For example, the OWL MC-2 (old World Labs) has the following manufacturer's specifications:
  Resolution: 100 nm;
  Precision: 100 nm mechanical and software capability;
  Accuracy: ±50 nm
  Repeatability: 99%
  Build Volume: 6×6×6 in
  Build Speed: 1 inch$^3$/hr.
  Build Materials: Photopolymer Additive manufacturing (AM) provides several advantages in manufacturing of the present device:
  (i) an entire device including projections and protrusions can be manufactured within a few hours;
  (ii) it can be used to precisely control the rigidity of different parts of the device (e.g. stems and leaves);
  (iii) any shape projection and/or protrusion can be manufactured to match any occlusion texture/composition;
  (iv) projection/protrusion shape and size can be matched to specific occlusion;
  (v) device or projection portion thereof could be printed in-hospital to match specific patient needs (e.g. vessel size, occlusion type).

Figure 6A:
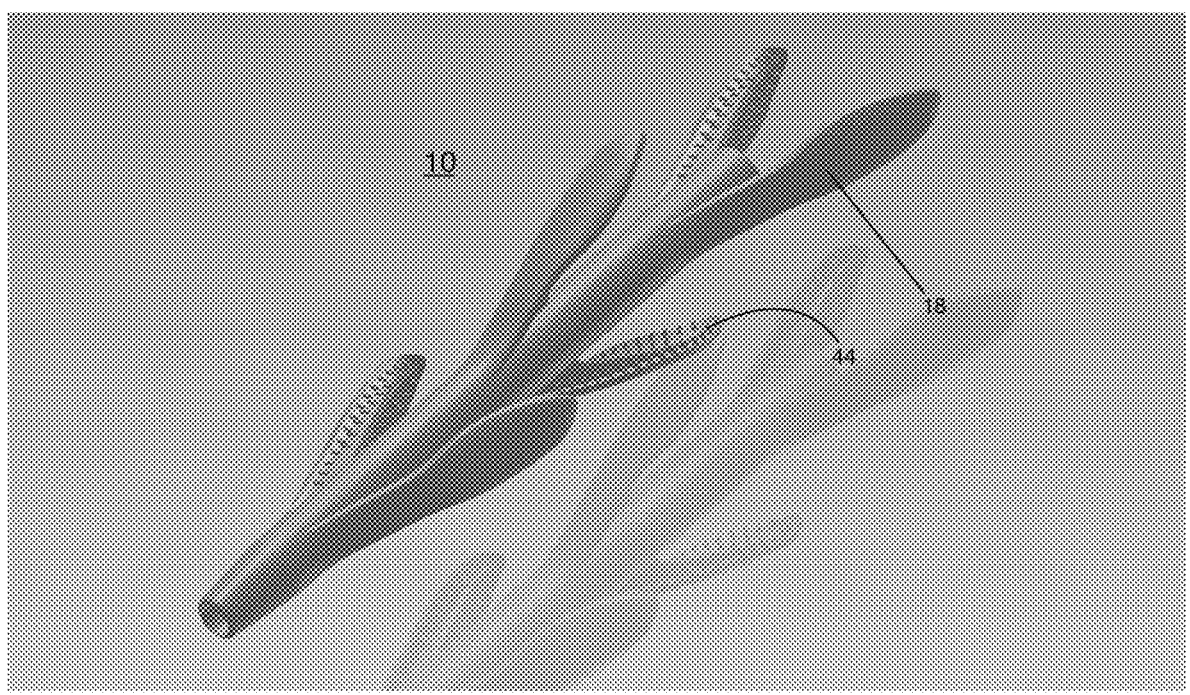
FIGS. 6a-c is a CAD drawing of a prototype device having conical projections with mushroom-shaped protrusions.
Figure 6B:
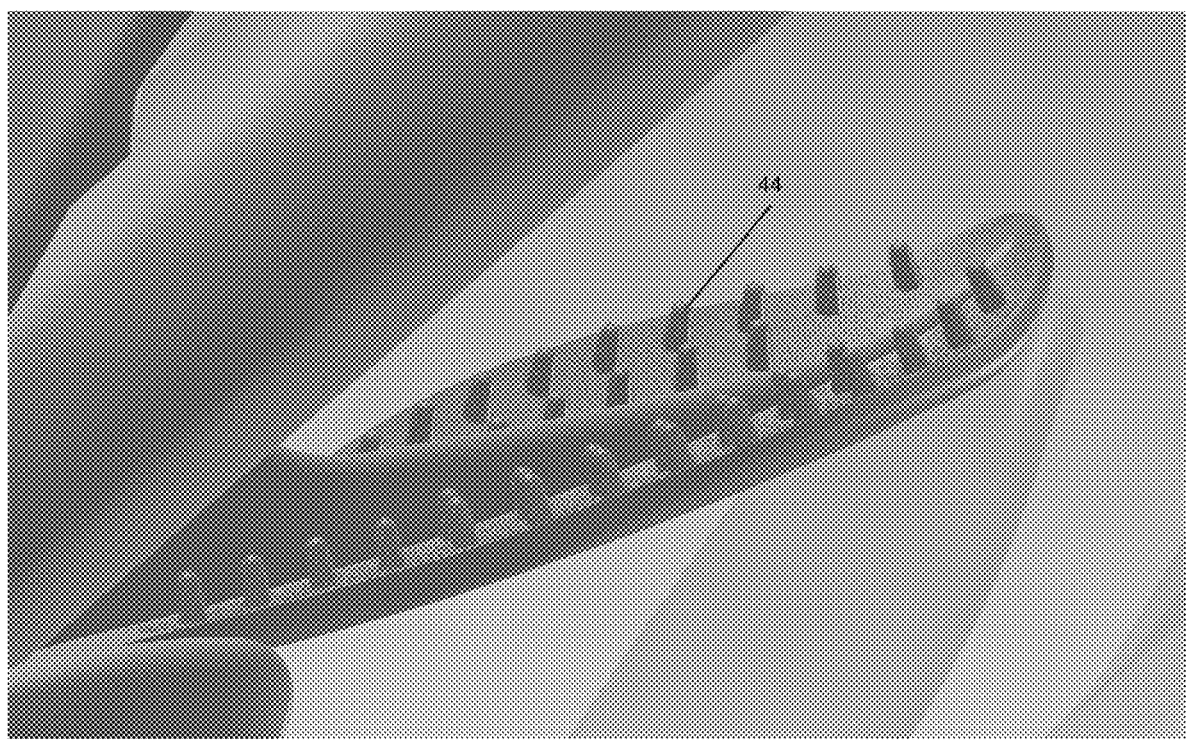
Figure 6C:
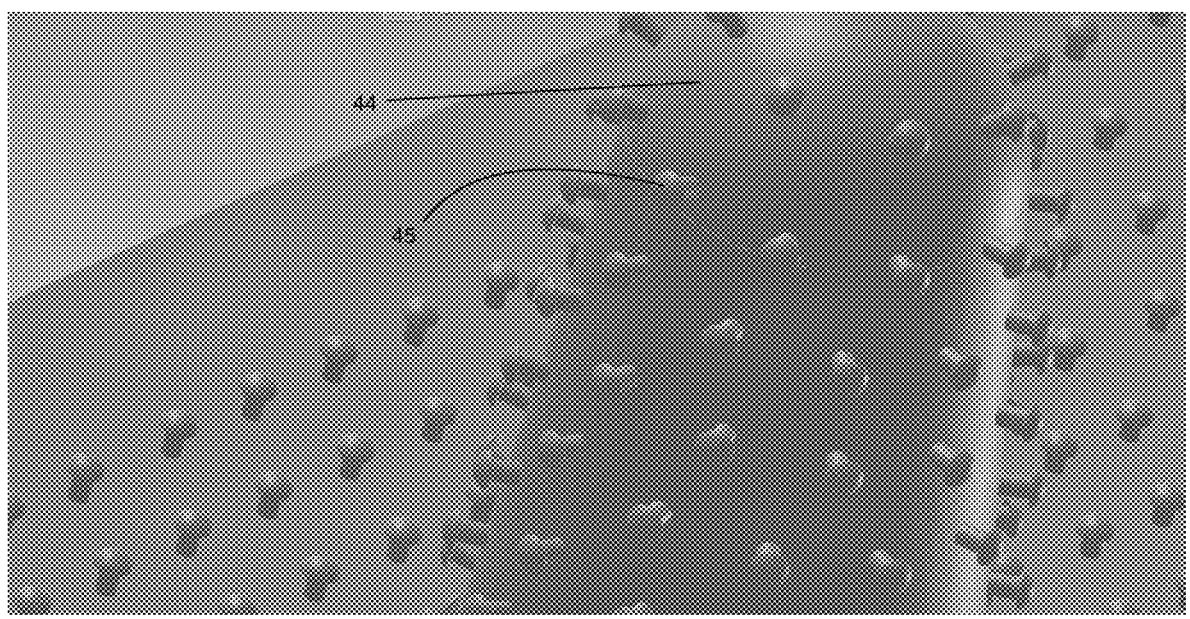

FIGS. 6a-c illustrate a configuration of the present device which is optimized for additive manufacturing.

The portion of the device shown in FIG. 6a includes a tube with 6 pairs of extensions (leaves). The tube and extensions are printed as a mono-structure and can be connected to a microcatheter for use (carrier tube can be fitted over a microcatheter). This specific design is optimized for removing occlusions in 2.5 mm blood vessels. The extension pairs are rotationally offset 90 degrees from each other to ensure optimized occlusion engagement and collection. The inner surface of each extension is manufactured with projections (44) which are conical in shape and are randomly yet homogenously distributed on the surface (FIG. 6b). Since these projections are 3D printed (along with the extension and carrier tube), exact structure and dimensions can be achieved. The diameter of the projections is 100 microns and the height 200 microns; average distance between projections is 300 microns. As is shown in FIG. 6c, each projection is 'printed' with surface protrusions (45) which are mushroom-shaped (stalk and cap with rounded mushroom 'cap') and are 4 microns in height, 2 microns in diameter (at base) and 3 microns in diameter (at top). Average distance between protrusions is 10 microns.

The size and shape parameters of the device shown in FIGS. 6a-c can be varied according to the occlusive material and patient. Occluding materials (e.g. blood clot in its various types, biological stones, foreign body and more) have different characteristics and physical/chemical properties which can vary from patient to patient. The size of the occluded vessel also varies from patient to patient.

Thus, in order to optimize engagement between the extensions of the present device and the occlusive material and optimize delivery and retrieval of the present device, the overall shape and size of the device as well as the shape and size of the extensions, projections and protrusions can be matched to the patient and/or occlusion.

The size of the vessel (diameter) and the shape, size and texture of the occlusive material can be determined from noninvasive imaging (including CT, MRI, Ultra Sound, Nuclear medicine and more); sampling (biopsy, microscopy) can be used to determine the composition of the occlusive material. Once the vessel size is determined and the occlusion is typed (size, shape, texture, composition), a suitable matching device design will be generated (including size and geometrical configuration or extensions, projections and protrusions) and printed using additive manufacturing.

This approach could be used in real time in a hospital setting to manufacture and employ a patient-specific device optimized for retrieving a specific occlusion in a specific vessel.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for retrieval of an occlusion in biological vessel comprising a plurality of extensions arranged around a distal portion of an elongated body, each extension of said plurality of extensions being leaf-like in shape and of solid construction with a length extending from said elongated body to a tip of said extension and an internal surface being concave along a width of said extension, said internal surface including an array of surface-mounted projections configured as hooks arranged in a circular pattern wherein said hooks are spaced 0.01-500 microns apart.

2. The device of claim 1, wherein only a portion of said internal surface of each of said plurality of extensions is covered by said array of surface-mounted projections.

3. The device of claim 2, wherein said portion is a proximal portion of said extension.

4. The device of claim 1, wherein said surface-mounted projections are angled with respect to said internal surface of each of said plurality of extensions.

5. The device of claim 4, wherein said angle is selected such that said surface-mounted projections penetrate the occlusion when said plurality of extensions are in contact with the occlusion and pulled proximally through the biological vessel.

6. The device of claim 1, wherein said extensions are capable of folding against said elongated body when advanced distally through the occlusion in the biological vessel.

7. The device of claim 1, wherein said extensions expand radially outward when the device is positioned within the occlusion in the biological vessel and pulled in a proximal direction.

8. The device of claim 1, wherein said extensions are composed of a first material and further wherein said surface-mounted projections are composed of a second material.

9. The device of claim 8, wherein said first material is softer than said second material.

10. The device of claim 1, wherein said extensions include an inward curving distal tip.

11. The device of claim 1, wherein the occlusion is a thrombus.

12. The device of claim 1, wherein said surface-mounted projections are 1-50 microns in length.

* * * * *